United States Patent [19]

Balding et al.

[11] Patent Number: 4,640,819

[45] Date of Patent: Feb. 3, 1987

[54] STRESS CRACK REDUCTION IN POLYCARBONATE PARTS

[75] Inventors: David P. Balding; Li-Chien Hsu, both of Mission Viejo; Lucas S. Gordon, Laguna Beach, all of Calif.

[73] Assignee: American Hospital Supply Corporation, Evanston, Ill.

[21] Appl. No.: 746,355

[22] Filed: Jun. 19, 1985

[51] Int. Cl.$^4$ ............................ A61L 2/08; A61L 2/20
[52] U.S. Cl. ............................................ 422/22; 422/1; 422/34; 29/458; 29/521
[58] Field of Search .......................... 422/1, 22, 34, 40; 174/110 V; 29/458, 521

[56] References Cited

U.S. PATENT DOCUMENTS 3,940,325  2/1976  Hirao ................................. 422/22
4,154,892  5/1979  Glatti et al. ................ 174/110 V X
4,222,379  9/1980  Smith ................................. 604/410
4,501,928  2/1985  Ishitobi ....................... 174/110 V X

FOREIGN PATENT DOCUMENTS 656699  1/1963  Canada .................................. 422/34

OTHER PUBLICATIONS

Modern Plastics Encyclopedia, 49, (1972), pp. 418–422, 463, 467.

Primary Examiner—Barry S. Richman
Assistant Examiner—J. Johnston
Attorney, Agent, or Firm—Weissenberger and Peterson

[57] ABSTRACT

Stress cracking of polycarbonate parts during prolonged storage while assembled with plasticized polyvinyl tubing is greatly reduced by using tubing in which tri-2-ethylhexyl trimellitate is the predominant or sole primary plasticizer.

9 Claims, No Drawings

STRESS CRACK REDUCTION IN POLYCARBONATE PARTS

FIELD OF THE INVENTION

This invention relates to a method of reducing stress cracking in polycarbonate parts which are preassembled with polyvinyl chloride tubing for marketing as sterile assemblies.

BACKGROUND OF THE INVENTION

Many types of disposable medical equipment (such as, for example, arterial filters for cardiopulmonary surgery) consist of rigid components (e.g. filter housings) which are assembled at the factory with flexible tubing, sterilized, and then marketed in assembled form in sterile packages which frequently remain on hospital shelves for a year or longer.

For a number of reasons including clarity, strength, flexibility, ease of application, bonding ability, and cost, the preferred material for the rigid parts of such assemblies is polycarbonate, while the preferred material for the flexible tubing parts is plasticized polyvinyl chloride (PVC).

Unfortunately, it has been discovered that stress cracks, ranging from minor surface crazing to extensive cracks deep enough to cause catastrophic failure of the part in use, tend to develop on the polycarbonate parts, sometimes during sterilization but more often during shipping and storage. It has now been found that the source of the problem is the slow migration along the surface of the polycarbonate parts of the phthalate plasticizers commonly used in the manufacture of commercial medical-grade PVC tubing. Contact of the plasticizer with areas that have been subjected to high molding stresses weakens the polycarbonate part in those areas and allows stress cracks to form. The problem is exacerbated by the alcohol or solvent lubricants and bonding agents which are typically used to facilitate assembly of the parts.

SUMMARY OF THE INVENTION

The invention greatly reduces the formation of stress cracks in polycarbonate parts assembled with PVC tubing by using PVC tubing in which most or all of the conventional di-2-ethylhexyl phthalate (DEHP) primary plasticizer has been replaced by tri-2-ethylhexyl trimellitate (TOTM). Although TOTM is also a known plasticizer (and therefore stress crack generator) for polycarbonates, TOTM-plasticized PVC is highly leachresistant and is not adversely affected in that respect by the commonly used isopropanol lubricant.

It is therefore the object of the invention to inhibit stress crack formation in polycarbonate parts assembled with PVC tubing for extended periods of time by using PVC tubing plasticized with TOTM.

DESCRIPTION OF THE PREFERRED EMBODIMENT

Assemblies used in surgery and other medical procedures are often marked in sterile packages in preassembled form. Where these assemblies need to be clearly transparent, as in the handling of blood in surgical environments, they typically consist of rigid polycarbonate parts with inlet and outlet nipples engaged by PVC tubing. During assembly, alcohols and solvents are typically used as lubricants and bonding agents to facilitate assembly of the parts. A typical sterilization procedure would call for exposure of the assembled parts to ethylene oxide gas at about 50°-60° C. for about 12 hours. Alternatively, the assemblies may be sterilized by about 2.9-3.3 Mrad of gamma radiation.

If conventional DEHP-plasticized medical-grade PVC tubing is used in the assembly, stress cracks gradually develop in the polycarbonate parts during shipping and storage of the sterile assemblies. The cracking is most pronounced in the vicinity of the PVC tubing but tends to progress along the surface of the polycarbonate part with the passage of time. The cracking is promoted by heat, and cracking already appears in some samples after sterilization.

To prevent such stress cracking, which has been discovered to be due to the migration of the relatively small DEHP plasticizer molecules from the PVC tubing along the surface of the polycarbonate part, assemblies constructed in accordance with the present invention use a special PVC tubing in which TOTM has been substituted for DEHP as the plasticizer. The large TOTM molecules have an exceedingly slow migration rate, even in the presence of isopropanol and/or solvents which substantially increase the leach rate of DEHP.

TOTM-plasticized PVC tubing compares favorably with conventional PVC tubing, particularly after ethylene oxide sterilization and irradiation, in terms of tensile strength, tear resistance, and pump head induced spallation. Although leaching of DEHP into blood is not a significant problem in most medical applications, it was observed that the leaching of plasticizer into blood was reduced by more than 95% through the use of TOTM-plasticized tubing.

Although other large-molecule plasticizers such as polyester and citrate plasticizers could be used to reduce migration, they are not satisfactory for other reasons. Polyester plasticizers, for example, are inefficient and provide less flexibility without sacrificing mechanical and physical properties.

In general, TOTM can be used in proportions ranging from about 20% to about 45% of the total tubing material weight, resulting in hardness values of about 90 to 60. The lower limit is dictated by excessive hardness of the tubing, and the upper limit by the lowering of the physical qualities of the tubing. Within these limits, the proportion of TOTM is not critical and should, for the most part, affect only the hardness of the tubing. In fact, by using varying proportions of secondary plasticizers such as epoxidized soybean oil (which is conventionally used to impart heat stability to PVC tubing), the proportion of TOTM can be varied to some degree without affecting the hardness of the tubing.

Where polycarbonate parts with large tolerances and gentle radii (hence with smaller internal molding stresses) can be used and a soft, pliable tubing of, say 60A hardness is desirable, a mixture of DEHP (which is a much more efficient plasticizer) and TOTM may be used as long as TOTM remains the dominant plasticizer.

Although the invention has been described herein in terms of TOTM, isomers of tri-2-ethylhexyl trimellitate (such as tri-n-octyl trimellitate) or other commercially available trimellitates such as tri-n-hexyl trimellitate or tri-n-decyl trimellitate may be used with the same effect.

EXAMPLE I

PVC tubing having an inner diameter of approximately 1 cm, a wall thickness of about 0.16 cm, and a Shore A hardness of 70 was extruded from a mixture containing about 55% medical-grade PVC resin, about 33% TOTM, about 11% epoxidized soybean oil, and a total of about 1% of various conventional extrusion processing aids such as lubricants. Following extrusion, the tubing was sterilized by exposure to ethylene oxide gas at about 55° C. for 12 hours, and by irradiation with about 3 Mrad of gamma radiation.

The tubing was cut into sections, and each section was assembled with a standard polycarbonate arterial filter housing by sliding the tubing over the inlet nipple of the filter to a distance of about 1.25 cm in the presence of isopropanol as a lubricant. Straps were tightened to a carefully controlled equal tightness about the tubing on the nipples to increase the stress in the nipples.

Sixteen filter housings were taken at random from a first production run (Batch A), and thirty housings from another production run (Batch B). One half of the Batch A and one-half of the Batch B assemblies were assembled as described above with the above-described TOTM-plasticized tubing, while the other half of each batch was assembled in the same manner with conventional DEHP-plasticized commercial medical-grade PVC tubing of the same size and hardness.

All the samples were allowed to stand for 3 hours to insure evaporation of the alcohol, and were then placed in an air-circulating oven at 65° C. for 15 hours. After the parts had cooled, the straps and tubing were removed, and stress cracks were visually observed.

The results were as follows:

| Batch | TOTM tubing | Conventional tubing |
| --- | --- | --- |
| A | No cracks | 3 no cracks |
|   |   | 5 slightly cracked |
| B | 4 no cracks | 1 moderately cracked |
|   | 9 very slightly cracked | 14 severely cracked |
|   | 2 slightly cracked |   |

In the foregoing tabulation, "very slightly cracked" indicates the appearance of isolated hairline surface cracks; "slightly cracked" indicates some surface cracking of essentially cosmetic effect; "moderately cracked" indicates the presence of sufficiently deep cracks to render the part unacceptable; and "severely cracked" indicates actually broken parts.

EXAMPLE II

Tubing similar to that of Example I was extruded from a mixture of about 55% medical-grade PVC resin, about 36% TOTM, about 8% epoxidized soybean oil, and about 1% processing aids. Shore A hardness of this tubing was also 70.

Eight test samples were produced by assembling sections of this tubing with polycarbonate filter housings as in Example I, using isopropanol lubricant and compression straps. Eight control samples from the same housing batch were produced in the same way but with conventional DEHP-plasticized medical-grade PVC tubing of the same size and hardness.

Following assembly, all the samples were humidified in air at about 40° C. and about 50% humidity for 18 hours. They were then sterilized for 9 hours in ethylene oxide gas at about 55° C. and allowed to aerate for 7 days at about 40° C. The entire humidification and sterilization process was then repeated to simulate a re-sterilization by the purchaser. The samples were then placed in an air-circulating oven at 65° C. for 15 hours to simulate extended storage. When the parts had cooled, the straps and tubing were removed, and the polycarbonate housings were visually inspected for cracks.

The results were as follows:

|      | After first sterilization | After 2nd sterilization | After 15 hrs. at 65° C. |
| --- | --- | --- | --- |
| TOTM | No cracks | 6 no cracks | 4 very slightly cracked |
|      |           | 2 very slightly cracked | 4 slightly cracked |
| DEHP | 4 no cracks | 2 no cracks | 1 moderately cracked |
|      | 4 slightly cracked | 5 slightly cracked | 7 severely cracked |
|      |           | 1 moderately cracked |   |

EXAMPLE III

Ten samples of the tubing of Example II were assembled with polycarbonate filter housings as described in Example I. Fifteen control samples from the same molding batch were assembled with conventional DEHP-plasticized medical-grade PVC tubing of the same size and hardness.

The samples were subjected to two successive heat treatments in an air-circulating oven at 65° C. for 15 hours each. After cooling, the straps and tubing were removed, and the samples were visually examined.

The results were as follows:

| TOTM | 2 no cracks |
| --- | --- |
|      | 6 very slightly cracked |
|      | 2 slightly cracked |
| DEHP | 1 moderately cracked |
|      | 14 severely cracked. |

EXAMPLE IV

Tubing could be prepared as in Example 1 from a mixture of about 45% medical-grade PVC, about 24% TOTM, about 20% DEHP, about 10% epoxidized soybean oil, and about 1% processing aids. The resulting tubing would have a Shore A hardness on the order of 60 but would still be expected to inhibit most of the plasticizer migration which would be present if the primary plasticizer were DEHP alone.

EXAMPLE V

Tubing could be prepared as in Example I from a mixture of about 62% medical-grade PVC, about 27% TOTM, about 10% epoxidized soybean oil, and about 1% processing aids. The resulting tubing would have a Shore A hardness on the order of 75, and it would be expected to produce comparison test results similar to those in Example I.

EXAMPLE VI

Tubing could be prepared as in Example I from a mixture of about 50% medical-grade PVC, about 38% TOTM, about 11% epoxidized soybean oil, and about 1% processing aids. The resulting tubing would have a Shore A hardness on the order of 66, and it would be expected to produce comparison test results similar to those in Example I.

EXAMPLE VII

Tubing could be prepared as in Example I from a mixture of about 57% medical-grade PVC, about 34% of a tri-n-hexyl trimellitate, about 8% epoxidized soybean oil, and about 1% processing aids. The resulting tubing would have a Shore A hardness on the order of 70 and it would be expected to produce comparison test results similar to those in Example I.

EXAMPLE VIII

Tubing could be prepared as in Example I from a mixture of about 53% medical-grade PVC, about 37% of a tri-n-octyl trimellitate or tri-n-decyl trimellitate, about 9% epoxidized soybean oil, and about 1% processing aids. The resulting tubing would have a Shore A hardness on the order of 70 and it would be expected to produce comparison test results similar to those in Example I.

We claim:

1. In a method of providing assemblies of polycarbonate parts which are in surface contact with polyvinyl chloride tubing, the improvement which comprises the step of reducing stress cracking in said polycarbonate parts by limiting the polyvinyl chloride tubing in contact therewith to plasticized polyvinyl chloride tubing produced using a trimellitate as the primary plasticizer.

2. The method of claim 1, further comprising the step of sterilizing said assembled tubing and parts in ethylene oxide gas for about 12 hours and at a temperature of about 50°–60° C.

3. The method of claim 1, further comprising the step of exposing said tubing and parts to about 3 Mrad of gamma radiation.

4. The method of claim 1, in which said primary plasticizer is selected from the group consisting of tri-2-ethylhexyl trimellitate and its isomers, tri-n-hexyl trimellitates and tri-n-decyl trimellitates.

5. The method of claim 4, in which said primary plasticizer is tri-2-ethylhexyl trimellitate or an isomer thereof.

6. The method of claim 5, in which said primary plasticizer is tri-2-ethylhexyl trimellitate.

7. In a method of providing assemblies of polycarbonate parts which are in surface contact with polyvinyl chloride tubing, the improvement which comprises the step of reducing stress cracking in polycarbonate parts by limiting the polyvinyl chloride tubing in contact therewith to plasticized polyvinyl chloride tubing produced using a trimellitate selected from the group consisting of tri-2-ethylhexyl trimellitate and its isomers, tri-n-hexyl trimellitates and tri-n-decyl trimellitates as the predominant primary plasticizer.

8. The method of claim 7, in which said predominent plasticizer is tri-2-ethylhexyl trimellitate or an isomer thereof.

9. The method of claim 8, in which said predominant plasticizer is tri-2-ethylhexyl trimellitate.

* * * * *